United States Patent
Wohlgemuth et al.

(10) Patent No.: US 6,556,859 B1
(45) Date of Patent: Apr. 29, 2003

(54) SYSTEM AND METHOD FOR CLASSIFYING SENSED ATRIAL EVENTS IN A CARDIAC PACING SYSTEM

(75) Inventors: Peter W. Wohlgemuth, Neukirchen (DE); Dave Munneke, Arnhem (NL); Gustaaf Stoop, Dieren (NL); Henk Westendorp, Zutphen (NL); Mattias Rouw, Arnhem (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/556,663

(22) Filed: Apr. 24, 2000

(51) Int. Cl.[7] .............................................. A61B 5/0452
(52) U.S. Cl. .......................................... 600/509; 607/9
(58) Field of Search ................................ 600/374, 509, 600/513, 515, 516, 517, 518, 519, 521; 607/4, 5, 9, 16, 119

(56) References Cited

U.S. PATENT DOCUMENTS

| | | | |
|---|---|---|---|
| 4,799,486 A | | 1/1989 | DuFault ................ 128/419 PG |
| 5,549,647 A | * | 8/1996 | Stoop et al. .................... 607/9 |
| 5,755,739 A | | 5/1998 | Sun et al. ...................... 607/14 |
| 5,778,881 A | * | 7/1998 | Sun et al. .................... 128/696 |
| 5,817,133 A | | 10/1998 | Houben .......................... 607/9 |
| 6,029,087 A | * | 2/2000 | Wohlgemuth .................. 607/9 |

* cited by examiner

*Primary Examiner*—George R. Evanisko
*Assistant Examiner*—Frances P. Oropeza
(74) *Attorney, Agent, or Firm*—Thomas F. Woods; Eric R. Waldkoetter; Tom G. Berry

(57) ABSTRACT

A system for a method of classifying distinct signals sensed from an electrode of an implantable cardiac pacing system positioned within an atrium of a heart of a patient is disclosed. The cardiac pacing system includes a pulse generator for generating pacing pulses and a controller for controlling the operation of a pacemaker. The method includes collecting atrial event signals consisting of P-wave signals and far field R-wave signals. An interim form factor histogram is generated based upon a form of collected atrial event signals. The interim form factor histogram includes an interim P-wave form factor histogram and an interim far field R-wave form factor histogram, each having bins of atrial event signals. A previously generated form factor histogram is weighted and combined with the interim form factor histogram to create a representative form factor histogram. The representative form factor histogram is analyzed to determine if a minimal safety margin is located between the representative P-wave form factor histogram and the representative far field R-wave form factor histogram. Atrial event signals are classified by form as either P-wave signals or far field R-wave signals based upon the representative form factor histogram.

29 Claims, 13 Drawing Sheets

| | Present P-Wave Form Factor Histogram | Present FFR-Wave Form Factor Histogram |
|---|---|---|
| + | Weighted Previous P-Wave Form Factor Histogram | Weighted Previous FFR-Wave Form Factor Histogram |
| = | Representative P-Wave Form Factor Histogram | Representative FFR-Wave Form Factor Histogram |

SYSTEM AND METHOD FOR CLASSIFYING SENSED ATRIAL EVENTS IN A CARDIAC PACING SYSTEM

THE FIELD OF THE INVENTION

The present invention relates to cardiac pacing systems capable of recognizing and classifying sensed cardiac signals. More specifically, the present invention relates to a signal classification system for recognizing and classifying P-wave signals and far field R-wave signals based upon a form of the signal through use of a form factor histogram.

BACKGROUND OF THE INVENTION

Implantable cardiac pacemakers have been devised which closely emulate the electrical activity of the heart. In such pacemakers, means are provided for sensing both atrial and ventricular depolarization signals and for generating pacing signals for both the atrium and the ventricle. The energy content of the QRS complex occurring during depolarization of the ventricle due to a R-wave signal is significantly higher than that of the P-wave signal, the R-wave or ventricle pacing spike often appears as a contaminate on the atrial sensing lead. Oversensing of the QRS on the atrial pacemaker lead is common.

Implantable cardiac pacemakers need to accurately process sensed signal information to determine when a genuine cardiac signal has in fact been sensed, and then to accurately identify, or classify, the signal. Separating cardiac signals from polarization effects and other noise artifact has always been a substantial problem in this field, and a great deal of effort has been placed on improving input circuits for this purpose. Additionally, it is often important to classify a sensed or acquired signal to determine whether the signal is, for example, a P-wave, a far field R-wave (FFRW), or an evoked response R-wave. Many prior art techniques have been developed for signal classification, but improvement is still needed.

One prior art technique is to establish a variable timing window, and classify the event in terms of a timing of a signal received during the window. However, early beats, estopic signals, etc. can fool such a technique, and noise can still mask the signal, which is sensed within the window. Other known techniques include morphology analysis, comparisons in the time and frequency domain, etc. While many of these techniques provide reasonably good results, they can involve considerable circuit complexity and frequently do not eliminate the probably of error due to detection of noise or other artifacts.

The advent of digital signal processing (DSP) has provided a tool, which can be very useful in the environment of an implantable medical device, such as an implantable cardiac pacemaker. In DSP technology, the incoming sense signal is converted to a digital signal, e.g., an 8-bit signal at a specified rate. Success of digital signals can be processed with high reliability, in a manner which is essentially hardware-controlled by the DSP circuitry. More recently DSP technology has advanced so as to provide the possibility of a low current chip, which can be used in an implantable cardiac pacemaker to provide significant sense signal processing capability.

The utilization of a DSP chip for an implantable cardiac pacemaker makes available an enhanced capacity of processing sensed signals, so as to enable more accurate classification of the signal. Such DSP processing, together with a microprocessor and an appropriate signal classification algorithm, provides a powerful tool for accurately sensing and classifying intercardiac signals. The patents listed in Table 1 are examples of different methods and systems for classifying and distinguishing sensed signals.

| U.S. Pat. No. | Inventor | Issue Date |
| --- | --- | --- |
| 4,799,486 | DuFault | 01/24/89 |
| 5,549,647 | Stoop et al. | 08/27/96 |
| 5,755,739 | Sun et al. | 05/26/98 |
| 5,817,133 | Houben | 10/06/98 |
| 6,029,087 | Wohlgemuth | 02/22/00 |

All patents listed in Table 1 above are hereby incorporated by reference herein in their respective entireties. As those of ordinary skill in the art will appreciate readily upon reading the Summary of the Invention, Detailed Description of the Preferred Embodiments, and claims set forth below, many of the devices and methods disclosed in the patents of Table 1 may be modified advantageously by using the teachings of the present invention.

In addition to the combined hardware and software capabilities discussed above, there is a need to provide an optimum decision algorithm for using the DSP-generated signal parameters so as to accurately and reliably classify sensed intercardiac signals. More specifically, there is a need for an optimum decision algorithm which can classify sensed signals as P-waves or far field R-waves based upon a form of the sensed signals.

SUMMARY OF THE INVENTION

The present invention overcomes the disadvantages of the prior art by providing a method of and system for classifying signals sensed from an electrode of an implantable cardiac pacing system positioned within an atrium of a heart of a patient.

The present invention has certain objects. That is, the present invention provides solutions to certain problems existing in the prior art such as: (a) an inability to classify atrial sensed signals based upon a form of the sensed signal; (b) an inability to generate a representative form factor histogram of sensed P-wave signals and far field R-wave signals; (c) an inability to distinguish P-wave signals from far filed R-wave signals through use of a form factor histogram; (d) an inability to control the operation of a pulse generator based upon a form factor histogram; (e) an inability to control parameters of an implantable cardiac pacing system via a computer readable medium; and (f) an inability to reject atrial event signals due to interference or unsettled conditions.

The system and method of the present invention provides certain advantages, including: (a) the ability to classify atrial sensed signals based upon a form of the sensed signal; (b) the ability to generate a representative form factor histogram of sensed P-wave signals and far field R-wave signals; (c) the ability to distinguish P-wave signals from far filed R-wave signals through use of a form factor histogram; (d) the ability to control the operation of a pulse generator based upon a form factor histogram; (e) the ability to control parameters of an implantable cardiac pacing system via a computer readable medium; and (f) the ability to reject atrial event signals points due to interference or unsettled conditions.

A system and method of the present invention has certain features, including a computer readable medium containing instructions for controlling a computer system. The instructions of the computer readable medium prompt the computer system to collect atrial event signals consisting of P-wave signals and far field R-wave signals. An interim form factor histogram is generated based upon a form of collected atrial event signals. The interim form factor histogram includes an interim P-wave form factor histogram and an interim far field R-wave form factor histogram, each having bins of atrial event signals. A previously generated form factor histogram is weighted and combined with the interim form factor histogram to create a representative form factor histogram. Atrial event signals are classified as P-wave signals or far field R-wave signals by form based upon the representative form factor histogram.

Another feature of the present invention is that collected atrial event signals are rejected if the pacemaker is not operating under normal conditions. Additionally, bins of atrial sensed events within the interim form factor histogram are discarded if a discard level is not met. Further, the representative form factor histogram is analyzed to determine if a minimum safety margin is present between the representative P-wave form factor histogram and the representative far field R-wave form factor histogram such that the form factor histogram includes two distinguishable classifications. Yet another feature of the present invention is that a controller controls the operation of a pulse generator of the cardiac pacing system based upon a form of the representative form factor histogram.

Other objects, advantages, and features of the invention will become apparent by referring to the appended drawings, Detailed Description, and claims.

DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
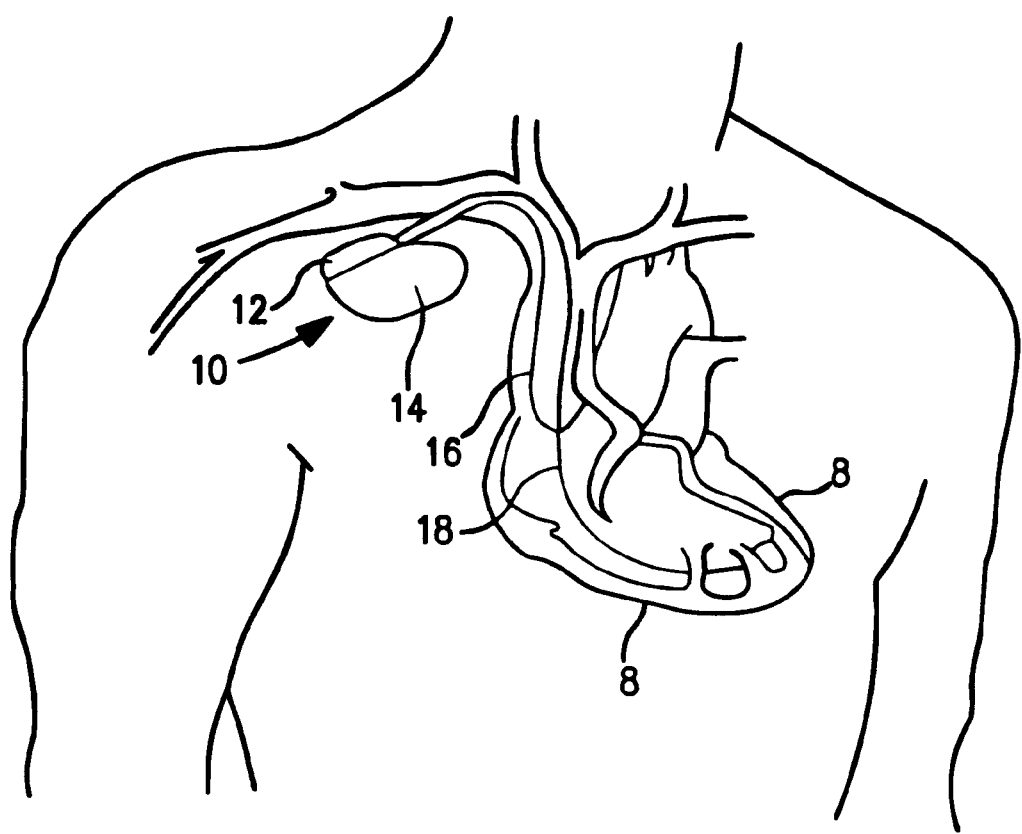
FIG. 1 is a simplified schematic view of one embodiment of an implantable medical device.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
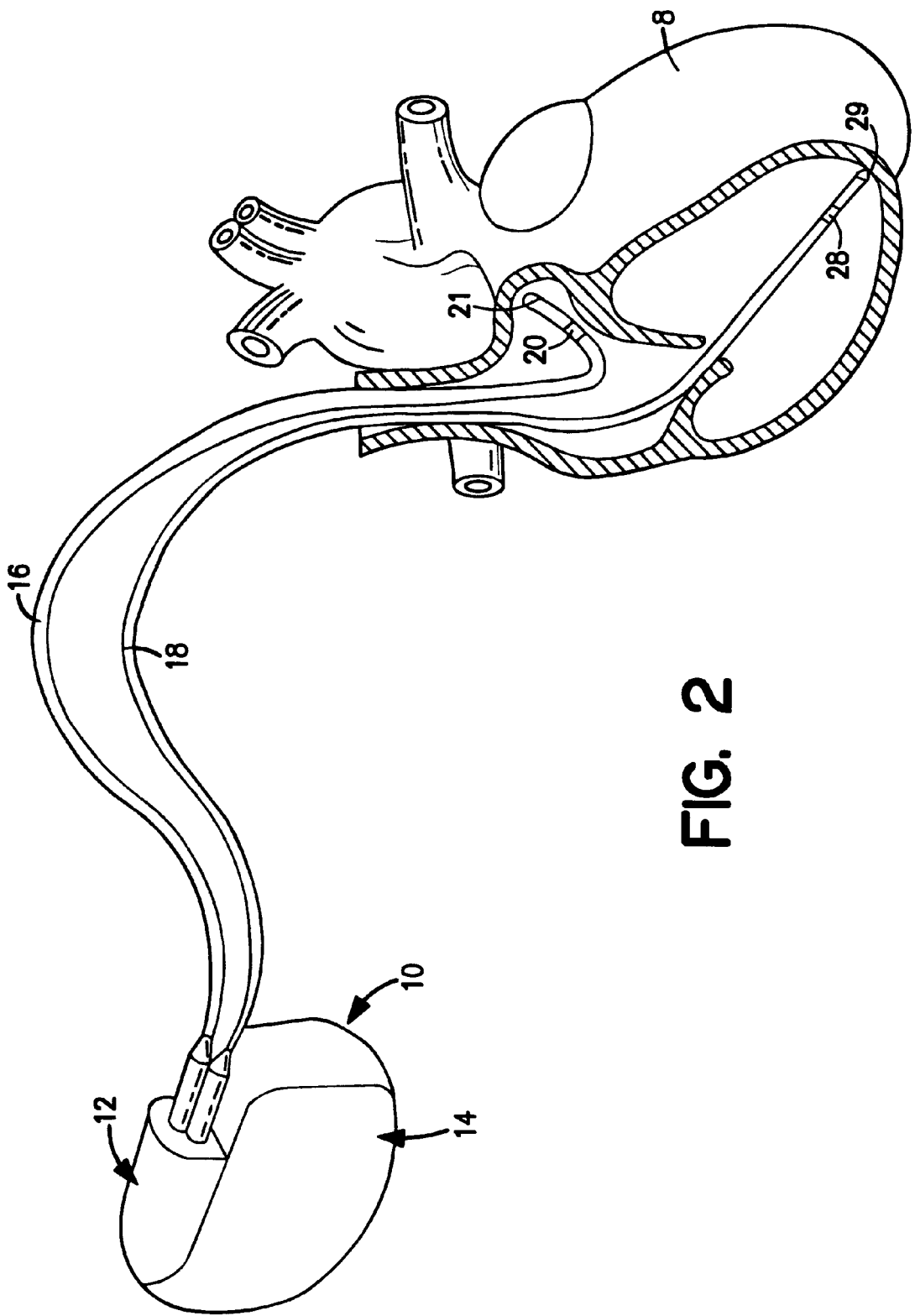
FIG. 2 is a simplified illustration of an implantable medical device with leads positioned within passageways of a heart.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
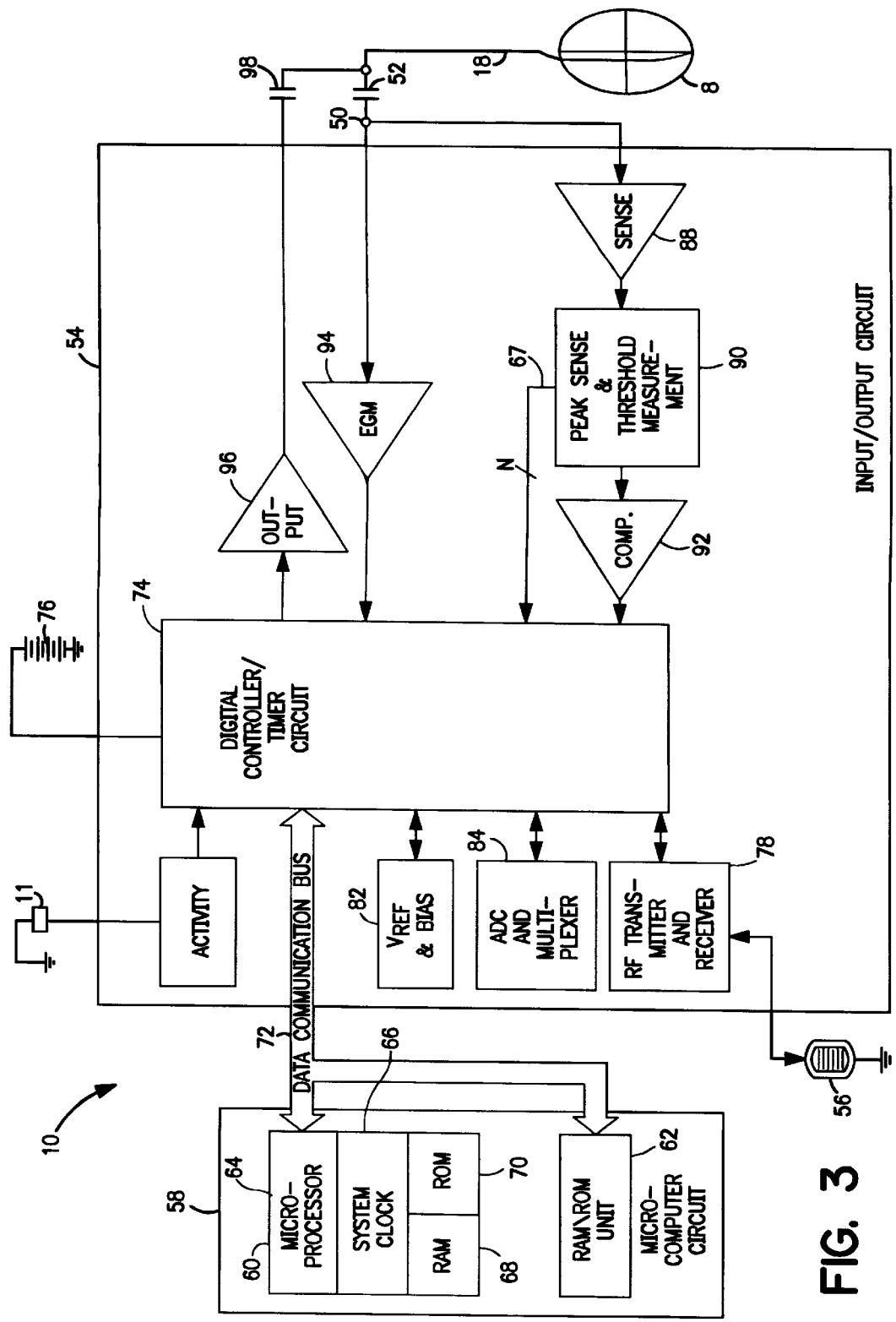
FIG. 3 is a block diagram illustrating the constituent components of an implantable medical device.

FIG. 3 shows a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multi-plexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all hereby incorporated by reference herein, each in its respective entirety.

Figure 4:
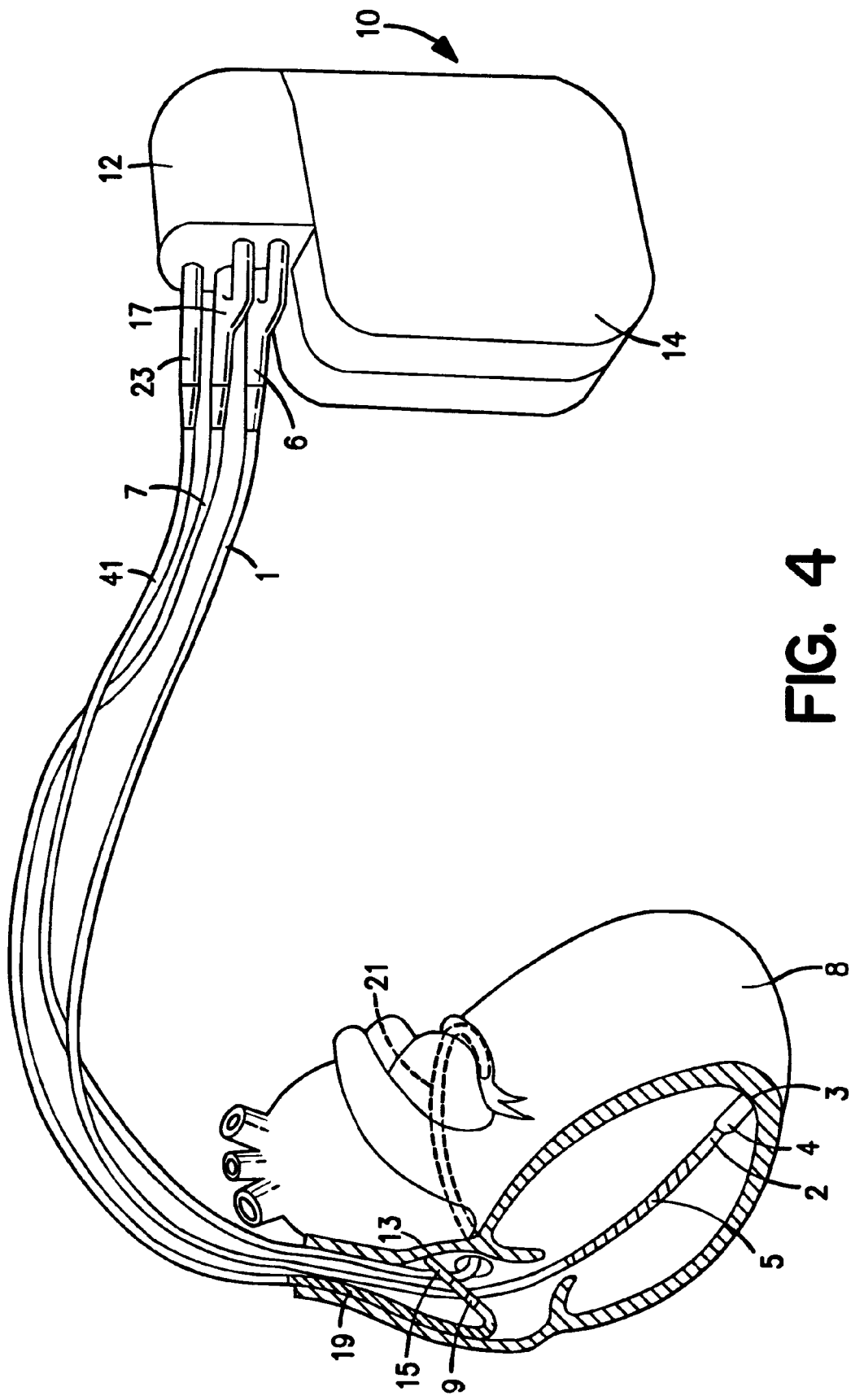
FIG. 4 is a simplified schematic view of an implantable medical device with leads positioned within passageways of a heart.
Figure 5:
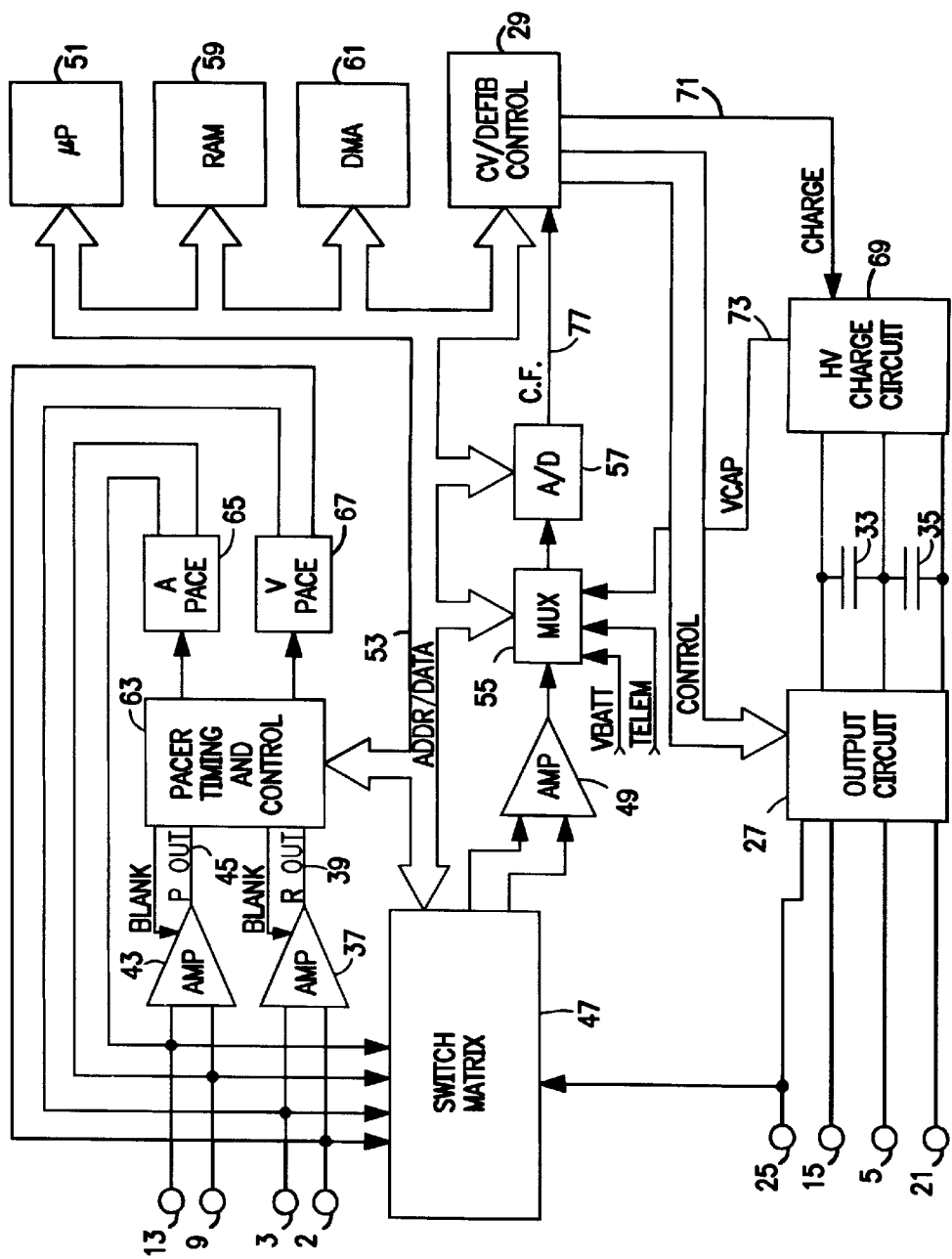
FIG. 5 is a partial block diagram illustrating one embodiment of an implantable medical device used in conjunction with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward-facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May-June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 27 under the control of control circuitry 29 via control bus 31.

Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Figure 6:
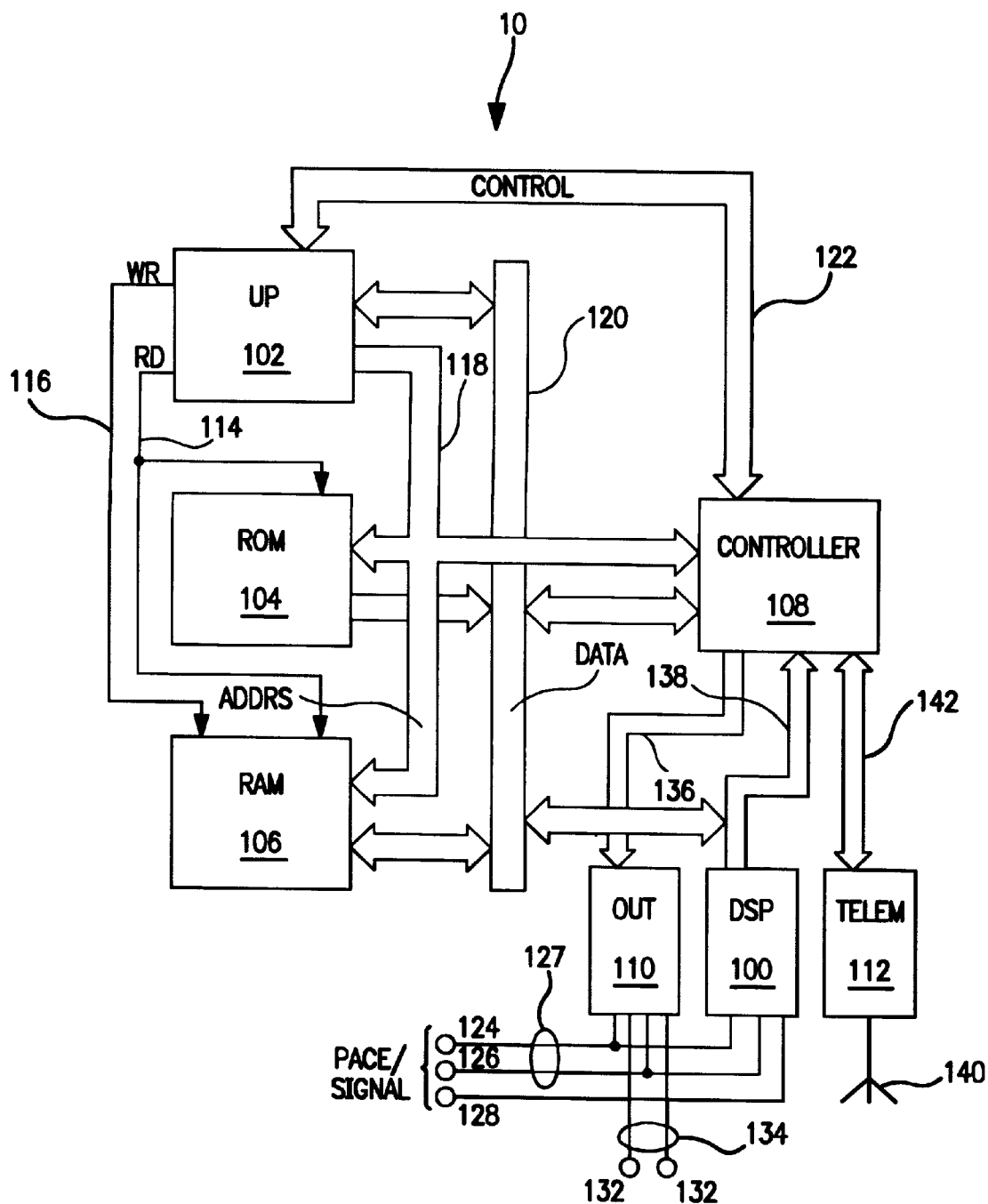
FIG. 6 is a block diagram showing the preliminary components of an implantable cardiac pacemaker in accordance with the present invention, illustrating the position of a DSP chip and a microprocessor in the overall scheme of sensed signal processing.

FIG. 6 is a block diagram showing the primary components of IMD 10 in accordance with the present invention, illustrating the position of digital signal processor (DSP) 100 and microprocessor 102 in the overall scheme of sensed signal processing. IMD 10, shown in FIG. 6, represents an implantable pacemaker of the type with which the present invention may be practiced. It is to be noted that FIG. 6 is represented as such a pacemaker and is not limiting to the actual architecture of the pacemaker. It is presented for the purpose of discussing data flow, and in particular, the position of DSP 100 and microprocessor 102 for purposes of sensing, analyzing, and classifying sensed intercardiac signals. Accordingly, FIG. 6 is considered to be exemplary rather than limiting with regard to the present invention. While the present invention is disclosed as embodied in a pacemaker, it is likewise applicable for incorporation in a cardioverter, combined cardioverter pacemaker, cardioverter defibrillator pacemaker, or any other implantable medical device. Further, while the discussion of FIG. 6 assumes a single chamber pacing system, it is understood that the invention is applicable to dual chamber and multi-chambered systems. For example, in a preferred dual chamber embodiment, DSP 100 has three channels, for respective processing of P-, R-, T-wave signals.

The primary elements of IMD 10 illustrated in FIG. 1 include DSP 100, microprocessor 102, read only memory 104, random access memory 106, digital controller 108, output amplifier 110, and telemetry/programming unit 112. Read only memory 104 stores the basic programming for IMD 10, including the primary instruction set defining the computations performed to drive the various timing intervals performed by IMD 10. Random access memory 106 serves to store the values of variable control parameters, such as programmed pacing rates, pulse width, and pulse amplitudes, which are programmed into IMD 10 by a physician. Reading from random access memory 106 and read only memory 104 is controlled by RD-line 114. Writing to random access memory 106 is controlled by WR-line 116. In response to a signal on RD-line 114, the contents of random access memory 106 or read only memory 104 designated by the then present information on address bus 118 are placed on data bus 120. Similarly, in response to a signal on WR-line 116, information on data bus 120 is written to random access memory 106 at the address specified by the information on address bus 118.

Digital controller 108 performs all of the basic timing and control functions of IMD 10. Digital controller 108 includes a pulse generator and at least one programmable timing counter initiated on paced or sensed contractions, for timing out intervals thereafter. This timing counter is used to define the escape interval for timing generation of pace pulses, as well as for timing the respective duration of the charge and recharge pulse portions of triphasic pulses. Digital controller 108 triggers output pulses to be generated and delivered from output amplifier 110, and generates interrupts on control bus 122 for cyclically waking microprocessor 102 from its sleep state to allow it to perform the required functions. One particular function of microprocessor 102 is to alter or change the signal processing characteristics of DSP 100, which is accomplished via data bus 120.

For a single chamber pacemaker, output amplifier 110 is coupled to electrodes 124 and 126 which are employed both for delivery of pacing pulses and for its sensing of cardiac signals. Electrode 124 is typically located on the distal tip end of an endocardial lead 127, and for ventricle pacing is preferably placed in the apex of the right ventricle. Conversely, for atrial pacing, electrode 50 is placed in the atrium of a patient. Electrode 126 is preferably a ring electrode as used with a bipolar lead. Electrode 128 represents the pacemaker housing, which may be used as the indifferent electrode for selected unipolar pacing and/or sensing operations. For a dual chamber or a multi-chamber pacing system, additional electrodes may be employed. For example, electrodes 130 and 132 carried by lead 134 may be used for pacing and sensing in the atrium, while electrodes 124 and 126 are used in the ventricle. Output amplifier 110 is controlled by digital controller 108 through bus 136 to determine the amplitude and pulse width of the pulse to be delivered and to determine which electrode pair is to be employed to deliver the pulse.

Cardiac signals are sensed at a desired pair or pairs of electrodes, in which bipolar and/or unipolar sensing may be employed. For "combipolar" sensing, a unipolar lead in the atrium and a unipolar lead in the ventricle are used, such that the signals are sensed by electrodes 130 and 132. Sense signals are inputted to DSP 100, which comprises a number of signal processing channels corresponding to signals of interest. For example, in a dual chamber pacemaker which incorporates P-wave processing either for rate control, capture detection, or other reasons, there are three channels for respective signal processing of the P-, R-, and T-waves. The data resulting from DSP 100 is transmitted via bus 138 through digital controller 108 and control bus 122 to microprocessor 102, for the signal classification operations, as well as any other necessary calculations.

External control of IMD 10 is accomplished via telemetry/programming unit 112, which allows communication between IMD 10 and an external programmer (not shown). Radio communication is typically employed via antenna 140. Appropriate telemetry/programming systems are well known in art, and the present invention is workable with any conventional telemetry/programming circuitry. Information entering IMD 10 from the programmer is passed to digital controller 108 via bus 142. Similarly, information form IMD 10 is provided to telemetry block 112 via bus 142 for transmission to the external programmer. Of importance to this invention, the classification algorithms for processing their parameters generated by each DSP channel can be reprogrammed in any known manner. In addition, IMD 10 may include one or more software program components capable of running on various elements of IMD 10. These software program components are capable of altering numerous variable parameters of IMD 10 and capable of classifying sense signals based upon various parameters.

Figure 7:
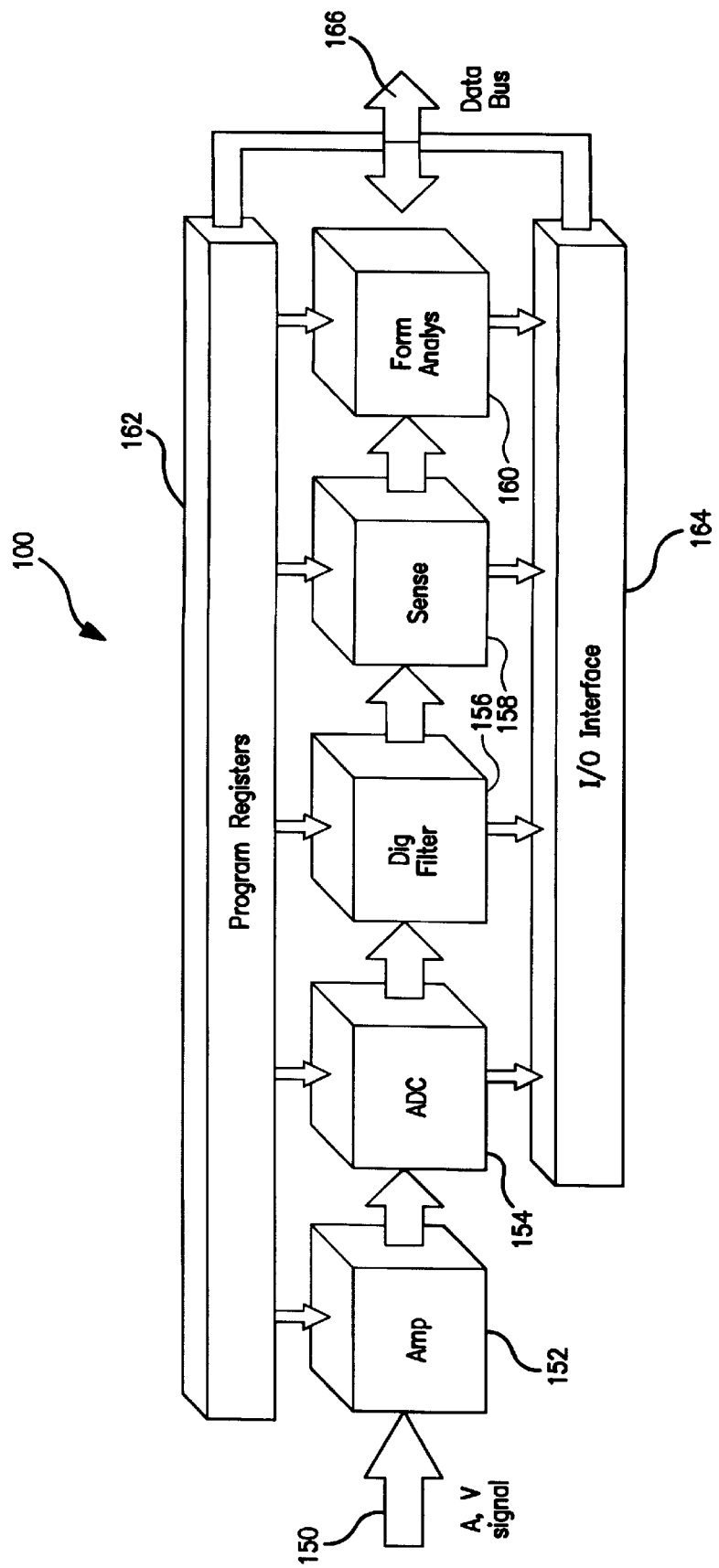
FIG. 7 is a block diagram illustrating the primary function and structure components of a DSP channel in accordance with the present invention.

FIG. 7 is a block diagram illustrating the primary functional and structural components of DSP 100 in accordance with the present invention. DSP 100 is manufactured with a chip area of approximately 20 mm$^2$ and draws approximately 0.7–1.5 microamps per channel. FIG. 7 shows atrial (A) or ventricular (V) signal 150 introduced into a DSP channel. It is understood that as many similar channels as desired are provided for signal processing of respective distinct signals. Signal 150, still in analog form, is first past through amplifier 152, having a filter characteristic in the range of approximately 0.7–500 hertz. The amplified analog signal is passed into analog/digital (A/D) converter 154, for generation of a digital signal. In one embodiment, the A/D conversion is suitable done by a delta-sigma modulator followed by a decimator to provide typically 8-bit bytes at 1.6 millisecond intervals. The digital signal from A/D converter 154 is passed to digital filter 156 which is suitably a digital bypass filter having a characteristic to eliminate both low frequency signal components and the offset of A/D converter 154. Digital filter 156 also removes high frequency artifacts. The output digital filter 156 is connected to sense block 158. Sense block 158 obtains the slew rate, or slope of the signal. The signal and slew rate of a signal are compared to predetermined plus and minus threshold voltages to derive a "sense" signal. The output of sense block 158 is input into form analysis 160.

Form analysis 160 represents one or more software programs or algorithms, discussed below in greater detail, which determine or "learn" the form of a particular signal, such as a P-wave signal or a far field R-wave signal, based upon the form of the particular signal. A form factor histogram of previous generated signals aides in this learning process. Form analysis 160 also classifies newly sensed signals based upon the form factor histogram of previous signals. For example, form analysis 160 can classify signals sensed by an electrode positioned in the atrium as either a P-wave signal or a far field R-wave signal. It is understood by those in the art that while form analysis 160 is shown as part of DSP 100, form analysis 160, representing a computer readable medium or algorithm may be located in a variety of components of IMD 10, such as microprocessor 102.

Program register 162 provides input to amplifier 152, A/D converter 154, digital filter 156, sense block 158, and form analysis 160. A/D converter 154, digital filter 156, sense block 158, and form analysis 160 are connected through input/output (I/O) interface 164 to data bus 166. Data bus 166 can connect either to data bus 138 (shown in FIG. 6) or to program registers 162. Program registers 162 serves a variety of purposes, such as programming amplifier sensitivity and programming threshold levels of the sense block, as well as other purposes understood by those in the implantable medical device field.

IMD 10 needs to accurately process sensed signal information from a heart of a patient to determine whether a general cardiac signal has in fact been sensed, and then to accurately identify, or classify, the signal. More specifically, it is important for IMD 10 to classify a sensed signal from an electrode positioned within the atrium of a patient to determine whether the sensed signal is either a P-wave signal or a far field R-wave signal. Numerous prior art techniques have been developed for signal classification, but improvement is still needed. The present invention utilizes a representative form factor histogram to classify sensed signals sensed within the atrium of a patient as either a P-wave signal or a far field R-wave signal based upon the form of the signal.

Far field R-wave sensing occurs when an electrode positioned within the atrium of a heart of a patient detects the electrical signal resulting from ventricle activation. For sensing left atrial activation via a coronary sinus lead, this problem is exaggerated since the lead is much closer to the ventricle which in addition has more muscle tissue. In some prior art pacemakers, a compromise between far field R-wave oversensing and P-wave undersensing is accepted. However, far field R-wave oversensing may result in false mode switching of the pacemaker, which in turn may evoke symptoms within the patient such as palpitations, fatigue, and pacemaker syndrome. To resolve the problem of far field R-wave oversensing, other prior art techniques revert to programming which utilizes lower sensitivity and longer post-ventricular atrial refractory periods (PVARP). However, this type of programming of a pacemaker may induce similar symptoms as far field R-wave oversensing due to P-wave undersensing. More particularly, high physiological rates may be obscured and low amplitude AF episodes may remain undetected.

The present invention provides an advance sensing method based upon form analysis of atrial events. Advantages of the present method include rejection of sensed far field R-waves through form analysis, which allow both high atrial sensitivity and short or no PVARP. Thus, the reliable suppression of far field R-wave sensing without rejection of real atrial events allows accurate rhythm interpretation.

Figure 8:
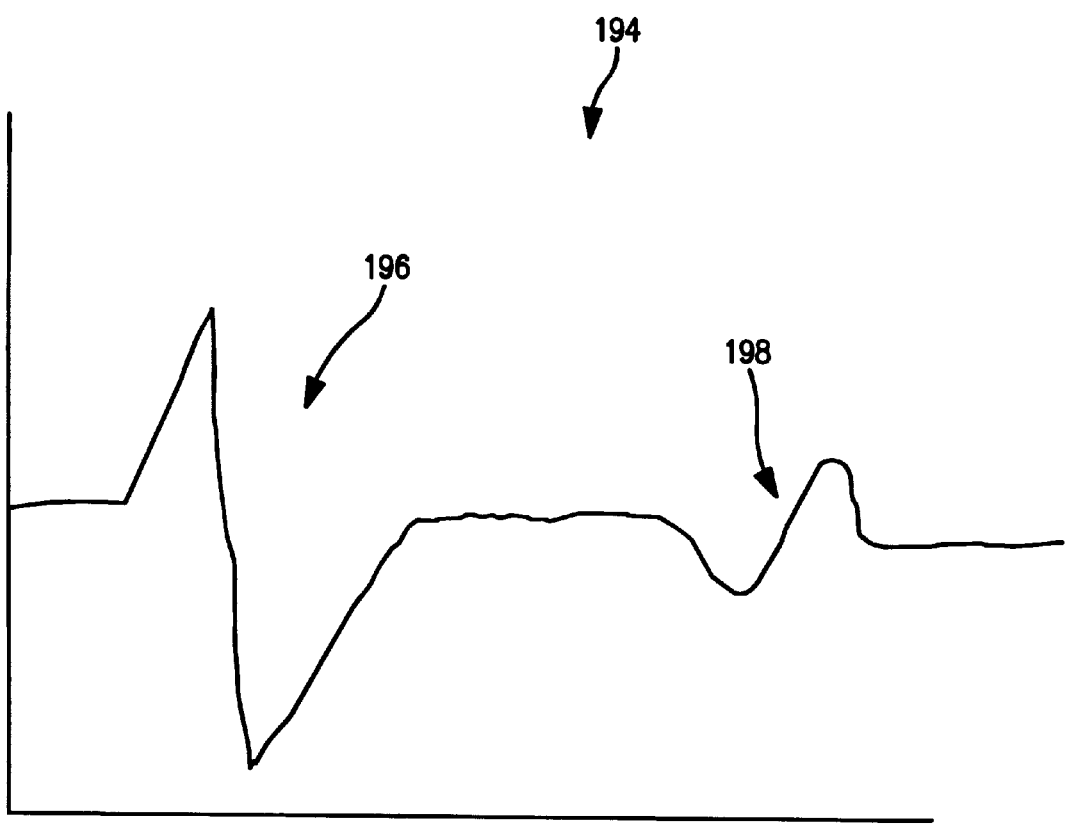
FIG. 8 is a graph illustrating a portion of a sensed signal from an electrode positioned within an atrium of a patient.

FIG. 8 is a graph illustrating a portion of a sensed signal sensed from 15 an electrode positioned within an atrium of a patient. Signal 194 includes P-wave signal portion 196 and far field R-wave section 198. The purpose of FIG. 8 is to illustrate the different form of the two signal portions and to illustrate the different location of the two signal portions.

Figure 12:
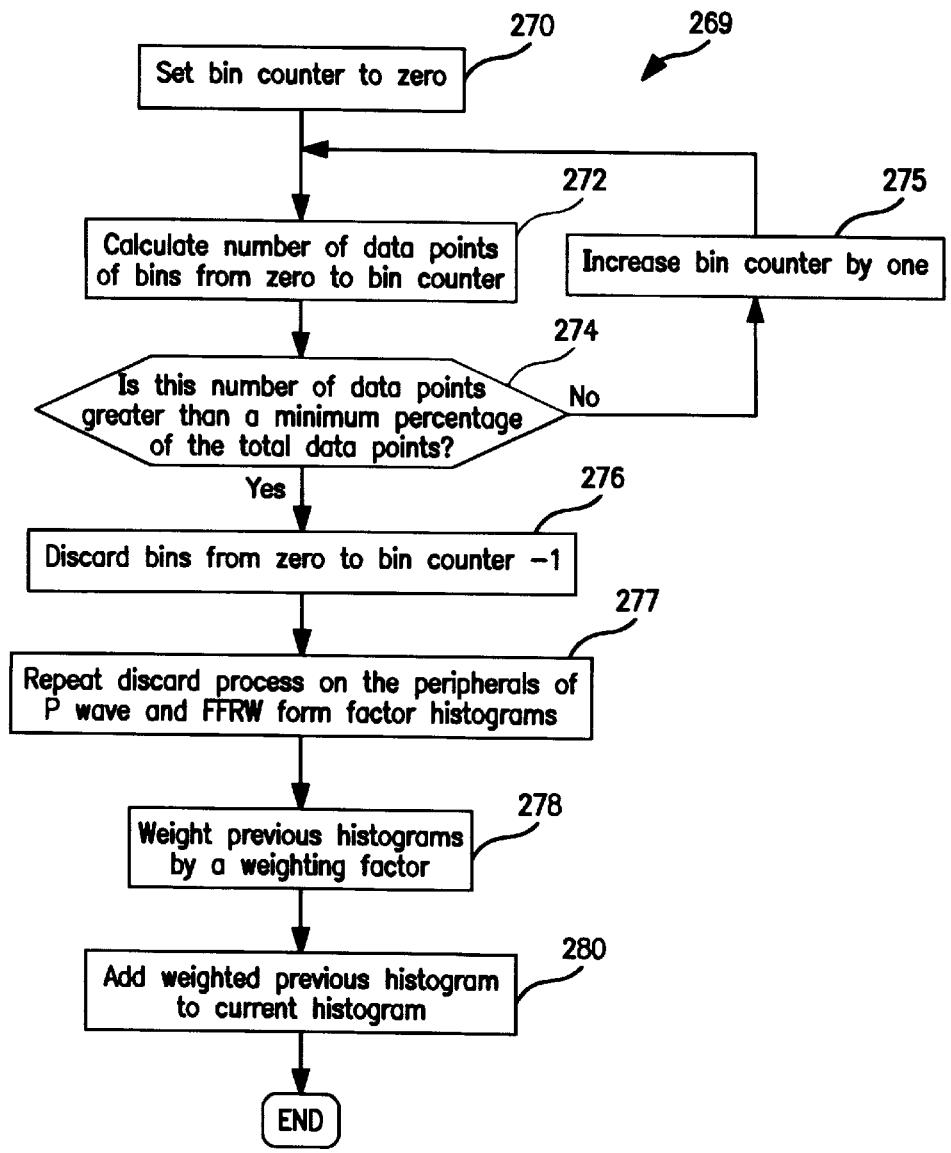
FIG. 12 is a flow chart illustrating various steps in the collection of data and formation of representatives form factor histograms.
Figure 13:
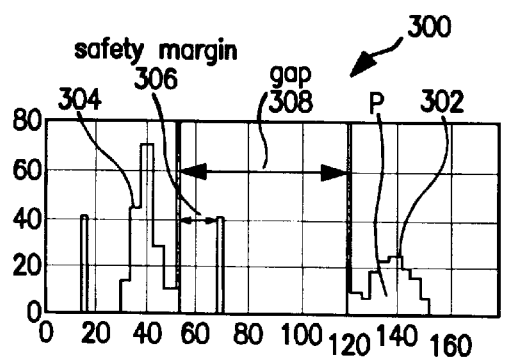
FIG. 13 is a graph illustrating a safety margin between a representative P-wave form factor histogram and a representative far field R-wave form factor histogram.
Figure 14:
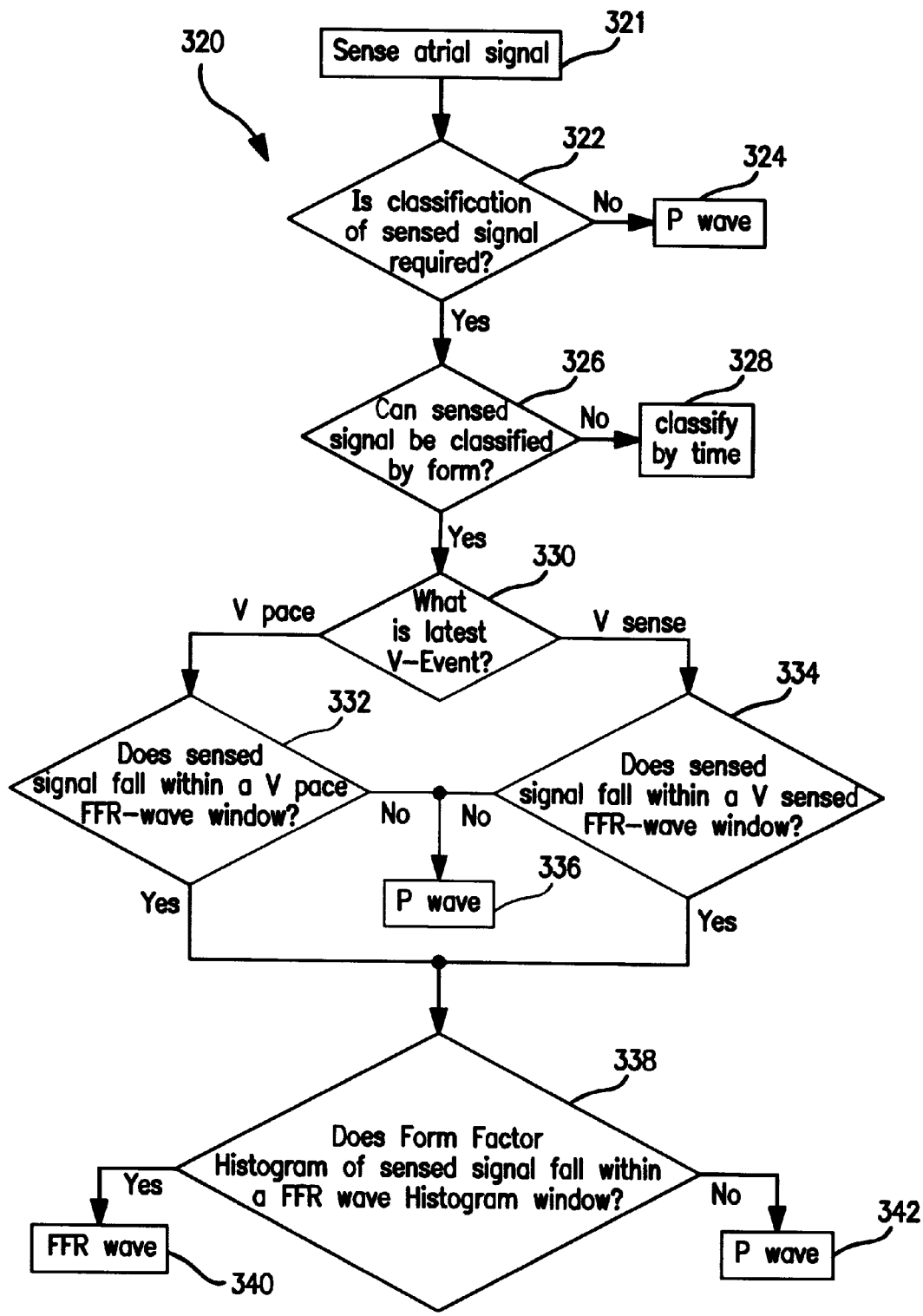
FIG. 14 is a flow chart illustrating a method of classifying atrial events by the form of the event.

The process and method of the present invention shown in FIGS. 9–13 illustrate the learning portion of the present invention, while the flow chart shown in FIG. 14 illustrates the classification process of the present invention. FIG. 9A is flow chart illustrating a data collection process necessary to generate interim form factor histograms for sensed P-waves and far field R-waves. In one preferred embodiment, flow chart 200 can be executed through use of an algorithm and a computer or server system, such as microprocessor 102 or form analysis block 160 of DSP 100.

In general, flow chart 200 illustrates a method of collecting data relating to P-waves and far field R-waves during a specified time interval. In one preferred embodiment, the time interval is in the range of approximately 5–10 days, and more preferably 7 days. Since classification is based upon learning over a representative time period, all situations of the patient are covered. Thus, the classification will be correct under all circumstances and reliably prevent far field R-wave sensing. In another preferred embodiment, "quick learning" may be utilized in which the update time interval is altered such that it is less than 5 days. In some circumstances, the update time interval may be as little as 30 minutes. During these 30 minutes, a physician may put a patient through a variety of exercises and/or situations in order to attempt to identify various sensed conditions.

The overall update time interval includes several sample time intervals. In one preferred embodiment, the sample time intervals have a length in the range of approximately 1–15 minutes, preferably 5–10 minutes. Once the sample time interval is completed, the data collected is forwarded to a memory device, which creates a form factor histogram. In one preferred embodiment, the form factor histogram is generated through use of computer software in the form of an algorithm.

At decision step 202 of flow chart 200 shown in FIG. 9, it is determined whether the timing of the system indicates a beginning of a sample interval. The remaining steps of flow chart 200 do not proceed until the beginning of a sample interval is indicated. Once the beginning of a sample interval is indicated, an analysis counter is set to 0, as shown at step 204. At decision step 206, it is determined whether an atrial event is detected within a predetermined time period. In one preferred embodiment, the predetermined time period is in the range of less than 2 minutes, preferably 1 minute. If an atrial event, such as the sensing of a signal, is not detected during the predetermined time period, IMD 10 is not operating under normal conditions since atrial events should be regularly detected. Thus, the algorithm reverts to decision step 202.

If an atrial event is detected during the predetermined time period, it is then determined whether IMD 10 is acting under well-known conditions of sinus rhythm of the patient. Data is rejected if any tachycardia or interference is present, as shown by decision steps 208 and 210. Likewise, data is rejected if IMD 10 is in an AV asynchronous state, as shown at decision step 212.

If no characteristics are identified which indicate abnormal conditions, the detected event is added to a corresponding interim form factor histogram, as shown at step 214. The analysis counter discussed in step 204 is then increased by a whole number, such as from 0 to 1, or 1 to 2, as shown at step 216. If analysis counter is equal to 0, the detected event in step 214 is added to an interim P-wave form factor histogram of an overall interim form factor histogram. Conversely, if the analysis counter described in step 204 is equal to 1, the detected event is added to an interim far field R-wave form factor histogram of an overall interim form factor histogram.

At decision step 218, it is determined whether the analysis counter is less than a maximum value. In one preferred embodiment, the maximum value equals 2. If the analysis counter is less than the maximum value, decision step 206 is repeated in order to detect another event. Conversely, if the analysis counter equals the maximum value, it is determined whether the sample time interval is less than a maximum sample time interval, as shown at decisions step 220. As previously discussed, in one preferred embodiment, the sample time interval is in the range of approximately 1–15 minutes. If the sample time interval is less than the maximum sample time interval, step 204 is repeated in which the analysis counter is set to 0. However, if the sample time interval is not less than the maximum sample time interval, it is determined whether an update time interval is less than the maximum update time interval, as shown in decision step 222. As previously discussed, in one preferred embodiment, the update time interval is in the range of 5–10 days. If the update time interval is less than the maximum update time interval, decision step 202 is repeated. However, if the update time interval is not less than the maximum update time interval, the collection of data as described in flow chart 200 is complete as shown at step 224.

Since classification is based upon learning over a representative time period, such as 5–10 days, all situations of the patient are covered. Therefore, the classification of sense signals later described will be correct under all circumstances and reliably prevent far field R-wave sensing. However, in one preferred embodiment, "quick learning" may be utilized in which the update time interval is altered such that it is less than 5 days. In some circumstances, the update time interval may be as little as 30 minutes. During these 30 minutes, a physician may put a patient through a variety of exercises and/or situations in order to attempt to identify various sensed conditions.

Figure 9A:
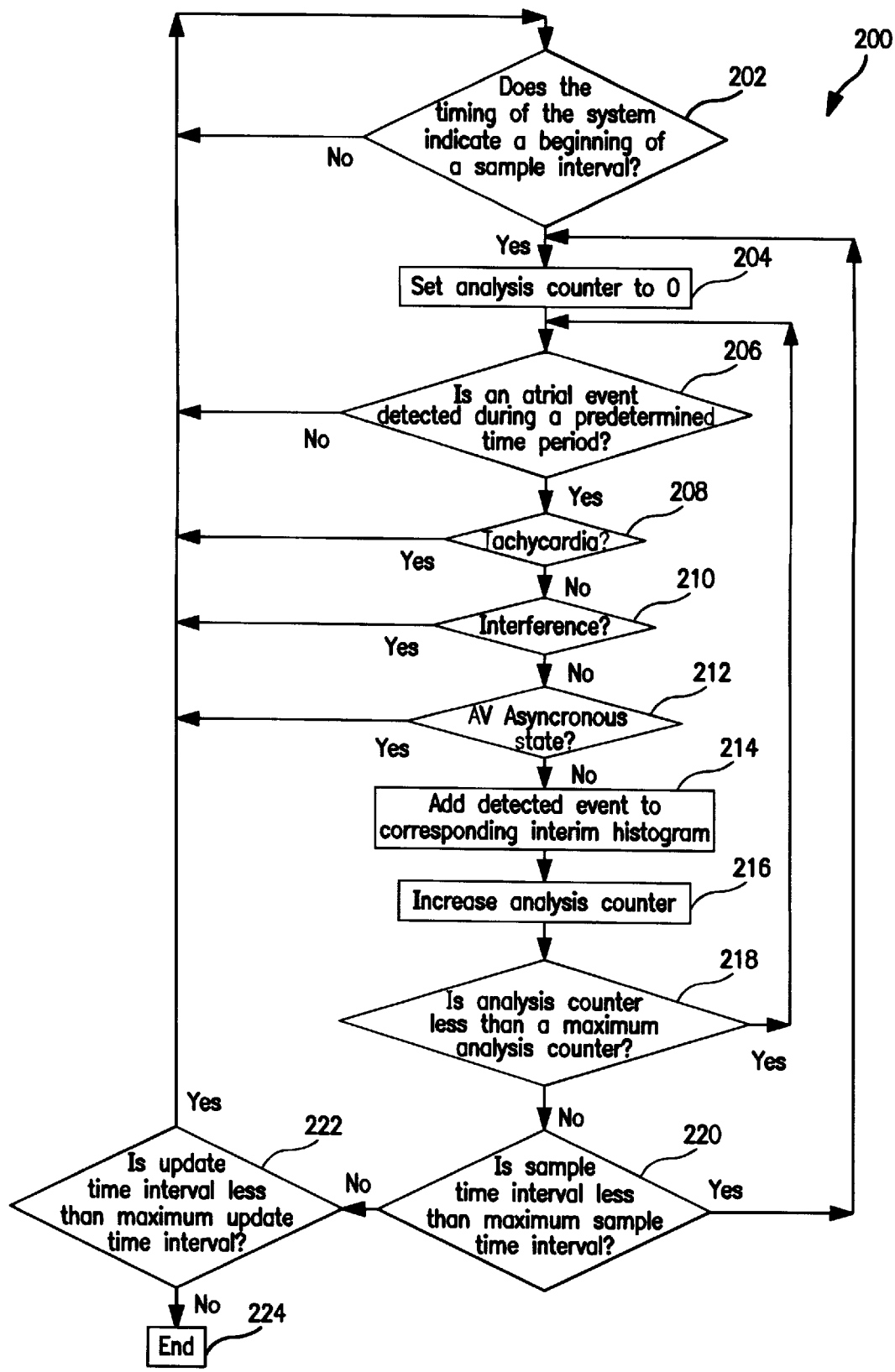
FIG. 9A is a flow chart illustrating the data collection process for P-waves signals and far field R-waves signals.
Figure 9B:
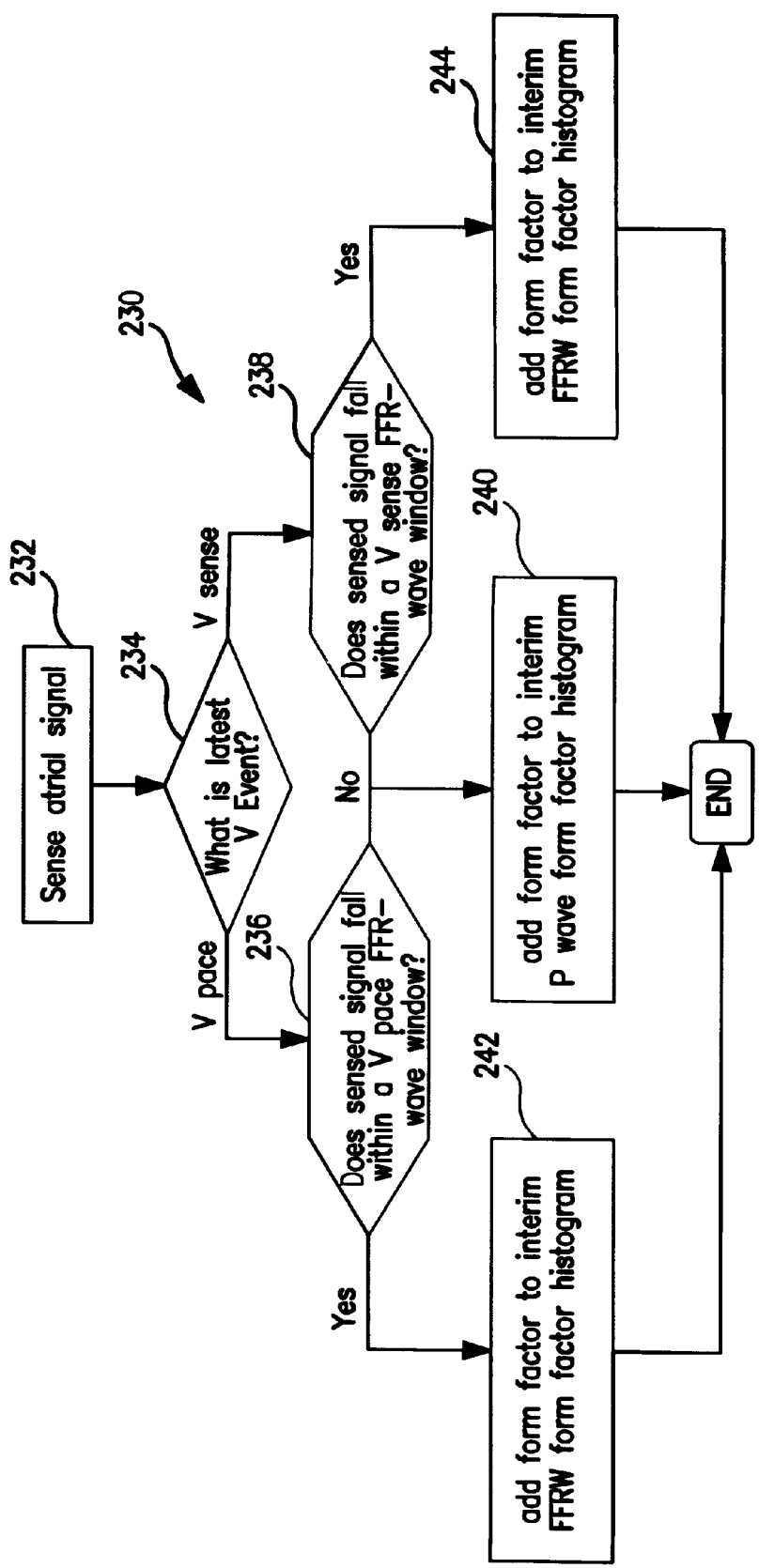
FIG. 9B is a flow chart illustrating the generation of P-wave and the far field R-wave form factor histograms.

FIG. 9B is a flow chart illustrating the generation of the P-wave and far field R-wave form factor histograms. At step 232 of flow chart 230, an atrial signal is sensed. At decision step 234, the latest ventricle event must be identified. Far field R-wave signals are signals which are generated within a ventricle of a patient which are sensed in the atrial of the patient. Therefore, the sensing of a far field R-wave signal in the atrial of a patient can only occur immediately after a ventricle event, such as a ventricle pace or a ventricle sense. Thus, at decisions steps 236 and 238, it is determined whether the sensed atrial signal falls within a ventricle pace far field R-wave timing window or a ventricle sense far field R-wave timing window, respectively. If the sensed atrial signal does not fall within either a ventricle pace far field R-wave timing window or a ventricle sense R-wave timing window, the form factor associated with the sensed atrial signal is added to an interim P-wave form factor histogram, as shown at step 240. However, if the sensed atrial signal falls within a ventricle pace far field R-wave timing window, the form factor associated with the sensed atrial signal is added to an interim far field R-wave form factor histogram, as shown at step 242. Similarly, if the sensed atrial signal falls within a ventricle sense far field R-wave timing window, the form factor associated with the sensed signal is added to the interim far field R-wave form factor histogram, as shown at step 244.

Figures 10, 11:
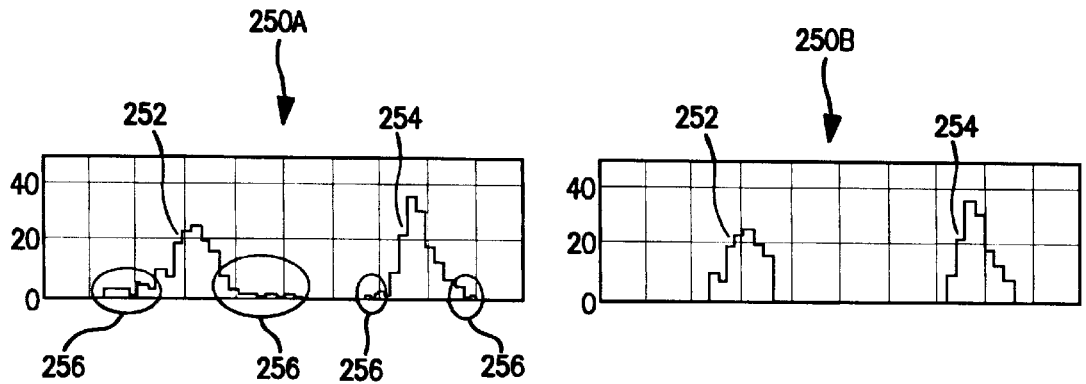
FIG. 10 includes two graphs illustrating a discard level of an interim form factor histogram.
FIG. 11 is a table illustrating the weighting and combination process of newly acquired interim form factor histograms with previously generated form factor histograms.

FIG. 10 includes two graphs illustrating a raw interim form factor histogram and an edited interim form factor histogram. Graphs 250A and 250B illustrate the inspection process undertaken on interim P-wave form factor histogram 252 and interim far field R-wave form factor histogram 254. The inspection process is necessary to eliminate or discard bins of data 256 which most likely contain non-accurate information. A discard level is predetermined such that it eliminates a total of less than approximately 10% of the data, preferably 5%, particularly eliminating bins located on the peripheral of the specific form factor histogram. Interim P-wave form factor histogram 252 and interim far field R-wave form factor histogram 254 are shown in graph 250B having all bins of data 256 which do not meet the discard level removed. Therefore, interim P-wave form factor histogram and interim far field R-wave form factor histogram 254 shown in graph 250B represent an accurate form of sensed P-waves and far field R-waves, respectively.

Interim P-wave form factor histogram 252 and far field R-wave histogram 254 shown in graph 250B are now ready to be combined with previously collected form factor histograms in order to update the overall form factor histogram corresponding to sensed P-waves and far field R-waves. However, it is desirous that the most recently collected data or form factor histograms be given more weight than earlier collected data or form factor histograms. Therefore, Table 260, shown in FIG. 11, illustrates the combination of interim form factor histogram information with previously detected form factor histogram information which includes a weighting component. As shown on the left side of Table 260, the present P-wave interim form factor histogram (show and discussed with reference to graph 250B of FIG. 10) is added to a previously generated form factor histogram including previous P-wave data. However, the previously generated P-wave form factor histogram is first weighted. In one preferred embodiment, the previously generated P-wave form factor histogram is multiplied by a factor in the range of approximately 0.25–0.90, preferably 0.50, and then added to the interim P-wave form factor histogram. Thus, a representative P-wave form factor histogram is generated which includes a greater emphasis on more recent interim P-wave form factor histograms, rather than older P-wave form factor histograms. As shown on the right side of table 260, the same calculations and analysis is done for far field R-wave form factor histograms to produce a representative far field R-wave form factor histogram.

FIG. 12 is a flow chart illustrating various steps in the collection of data and formation of form factor histograms. It is understood by those in the art that the flow chart shown in FIG. 12 can be executed in any of a variety of known waves, such as through the use of a computer or server system or systems in conjunction with a software program or algorithm.

At step 270 of flow chart 269, a bin counter is set to 0. The number of data points of bins from zero to the bin counter is calculated, as shown at step 272. At decision step 274, it is determined whether the number of data points is greater than a minimum percentage number of the total data points. More specifically, the number of data points within a particular bin is compared to a discard level. If the number of data points within a particular bin does not exceed the discard level, the particular bin of data points is discarded, as shown at step 276 of FIG. 12. Once the bins of data which do not reach the discard level are discarded, the interim form factor histogram shown in FIG. 10 at 250B remains. However, if the number of data points is not greater than a minimum percentage of the total data points, the bin counter is increased by one (step 275) and step 272 is repeated.

At step 277, the above-discussed discard process is repeated on the peripherals of the interim P-wave and far field R-wave form factor histograms. At step 278, the previously generated form factor histograms for a P-wave signal and a far field R-wave signal which represents previously collected data are weighted by a weighting factor. As previously discussed, in one preferred embodiment, the weighing factor is in the range of approximately 0.25–0.90, preferably 0.50. At step 280, the weighted previously generated form factor histogram is added to the current interim form factor histogram to create a representative form factor histogram for the particular signal of interest, such as a P-wave signal or a far field R-wave signal.

FIG. 13 shows graph 300 which illustrates safety margin 306 between representative P-wave form factor histogram 302 and representative far field R-wave form factor histogram 304. If representative R-wave form factor histogram 304 does not contain data or contains a very small number of data points, discrimination of far field R-wave sensing is not needed for this patient. In other words, if far field R-wave form factor histogram 304 contains a minimal number of bins of data points, the sensed far field R-waves can be ignored since they do not materially affect the sensing of P-waves and do not adversely affect the programming of IMD 10.

In one preferred embodiment, discrimination of far field R-waves sensing is not needed for a patient in which less than 300 data points are included in far field R-wave form factor histogram 304, preferably less than 100 data points. In an average patient, approximately 1,600 data points can be collected during a 7-day period. It is understood that the number of required data points or bins may be altered to coincide with varying overall update time intervals without deviating from the present invention.

If discrimination is needed, classification by form is preferred over classification by time since classification by form does not require the blanking of an electrode. Classification by time does require blanking of an electrode to gather information. In other words, by using classification by form, the signal to one or electrodes of IMD 10 does not have to be interrupted such that data points relating to a second electrode receiving a signal from IMD 10 are calculated. Various references disclose different methods for classifying P-wave signals and far field R-wave signals by time, such as U.S. Pat. No. 5,549,647 to Stoop et al. entitled, "Pacemaker with Improved Far Field R-Wave Sensing and Suppression."

A requirement of utilizing classification by form to classify P-wave signals and far field R-wave signals is that a safety margin, such as safety margin 306 shown in FIG. 13, must be present between representative P-wave form factor histogram 302 and representative far field R-wave form factor histogram 304. It is understandable that there must be some separation between representative P-wave form factor histogram 302 and representative far field R-wave form factor histogram 304 such that each form factor histogram has a specific form or shape. Overlap of form factor histograms indicates that classification by form is not applicable. In one preferred embodiment, safety margin 306 must be greater than one bin width, and preferably greater than two bin widths. Similarly, in one preferred embodiment, the required gap size for gap 308 is typically greater than two bin widths, and preferably greater than four bin widths.

FIG. 14 is a flow chart illustrating a method of classifying an atrial event by the form of the event. The method begins by sensing an atrial signal or event, as shown at step 321. At decision step 322, it is determined whether classification of a sense signal is required. Depending upon lead locations and strength of signals, some IMDs do not sense far field R-waves. In these circumstances, classification of sense signals is not required, and each signal is, by default, classified as a P-wave, as shown at step 324. However, if classification of a sense signal is required, it is determined whether the classification can be determined through use of a form factor histogram, as shown at decision step 326. A sense signal may not be classified by form if the representative form factor histogram, such as that shown in FIG. 13, does not include gap 308 or safety margin 306, indicating that there is an overlap or a near overlap between representative P-waves form factor histogram 302 and representative far field R-wave form factor histogram 304. In this circumstance, the sensed atrial signal must be classified by time, as shown at step 328. There are various methods to classify atrial signals by time, one of which is disclosed in U.S. Pat. No. 5,549,647 to Stoop et al. entitled, "Pacemaker with Improved Far Field R-Wave Sensing and Suppression."

If the sensed atrial signal can be classified by form, decision step 330 dictates that the latest ventricle event must be identified. Far field R-wave signals are signals which are generated within a ventricle of a patient which are sensed in the atrial of the patient. Therefore, the sensing of a far field R-wave signal in the atrial of a patient can only occur immediately after a ventricle event, such as a ventricle pace or a ventricle sense. Thus, at decisions steps 332 and 334, it is determined whether the sensed atrial signal falls within a ventricle pace far field R-wave window or a ventricle sense far field R-wave window, respectively. If the sensed atrial signal does not fall within either a ventricle pace far field R-wave window or a ventricle sense R-wave window, the sensed atrial signal is classified as a P-wave, as shown at step 336. More specifically, if the sensed atrial signal does not fall within a specific time frame after a ventricle event, such as a ventricle pace or a ventricle sense, the sensed atrial event is classified as a P-wave.

If the sensed atrial signal does fall within a ventricle pace far field R-wave window or a ventricle sense far field R-wave window, it is determined whether the form factor of the sensed atrial signal falls within a representative far field R-wave form factor histogram, as shown at decisions step 338. The formation of the representative far field R-wave form factor histogram has previously been discussed in great detail. If the form factor of the sensed atrial signal falls within the boundaries of a representative far field R-wave histogram, the sensed atrial signal is labeled as a far field R-wave, as shown at step 340. Conversely, if the form factor of the sensed atrial signal does not fall within a representative far field R-wave form factor histogram boundary, but rather falls within a representative P-wave form factor histogram, the sensed atrial signal is classified as a P-wave, as shown at step 342.

In summary, the present invention provides a system and method for determining or learning the characteristics of P-waves and far field R-waves via form factor histograms and classifying sense signals as either P-waves or far field R-waves based upon the learned or determined characteristics of these waves. Therefore, proper controlling or programming the operation of a pulse width generator or microprocessor of IMD 10 may be achieved.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to cardiac pacemakers per se, but may find further application in any implantable medical device. The present invention further includes within its scope of making and using cardiac pacing system which includes means for classifying sensed atrial signals as either P-wave signals or far field R-wave signals described herein above and means for controlling subcomponents of IMD 10 to ensure proper pacing and sensing.

In the claims, means-plus-function clauses are intended to cover the structures described herein as performing the recited function and not only structural equivalence but also equivalent structures. Thus, although a nail and a screw may not be structural equivalence in that a nail employs a cylindrical surface to secure wooden parts together, whereas a screw employs a helical surface, an environment of fastening wooden parts a nail and a screw are equivalent structures.

All printed publications, patent applications and patents referenced hereinabove are incorporated by reference herein, each in its respective entirety.

What is claimed is:

1. A method of classifying signals sensed by an electrode of a medical electrical lead adapted to be positioned within an atrium of a heart of a patient, the lead forming a portion of a cardiac pacing system further comprising an implantable pulse generator for generating pacing pulses, the method comprising:

collecting atrial event signals consisting of P-wave signals and far field R-wave signals;

rejecting atrial event signals if the pulse generator is not operating under normal conditions;

generating an interim form factor histogram based upon a form of collected atrial event signals which, the interim form factor histogram including an interim P-wave form factor histogram and an interim far field R-wave form factor histogram, each having bins of atrial event signals;

discarding bins of atrial event signals within the interim form factor histogram which do not meet a discard level;

weighting a previously generated form factor histogram including a previously generated P-wave form factor histogram and a previously generated far field R-wave form factor histogram;

combining the weighted previously generated form factor histogram with the interim form factor histogram to create a representative form factor histogram;

determining if a minimal safety margin is located between a representative P-wave form factor histogram and a representative far field R-wave form factor histogram within the representative form factor histogram; and classifying atrial event signals as either P-wave signals or far field R-wave signals based upon the representative form factor histogram.

2. The method of claim 1, wherein collecting atrial event signals further comprises:

collecting atrial event signals consisting of P-wave signals and far field R-wave signals for a time interval in the range of 5–10 days.

3. The method of claim 1, wherein collecting atrial event signals further comprises:

collecting atrial event signals consisting of P-wave signals and far field R-wave signals for a time interval for approximately 30 minutes.

4. The method of claim 1, wherein rejecting atrial event signals further comprises:

rejecting atrial event signals if a tachycardia condition is sensed by the pulse generator.

5. The method of claim 1, wherein rejecting atrial event signals further comprises:

rejecting atrial event signals if interference is present within the pulse generator.

6. The method of claim 1, wherein rejecting atrial event signals further comprises:

rejecting atrial event signals if the pulse generator is operating in an AV asynchronous state.

7. The method of claim 1, wherein discarding bins of atrial event signals further comprises:

discarding bins of atrial events signals within the interim form factor histogram which do not meet a discard level such that approximately 0%–10% of the collected atrial event signals are discarded.

8. The method of claim 1, wherein weighting a previously generated form factor histogram further comprises:

multiplying a previously generated form factor histogram by a factor in the range of 0.25–0.90.

9. The method of claim 1, wherein weighting a previously generated form factor histogram further comprises:

multiplying a previously generated form factor histogram by a factor of 0.50.

10. The method of claim 1, wherein determining if a minimum safety margin is located between a representative P-wave form factor histogram and a representative far field R-wave form factor histogram further comprises:

determining if at least a single bin width is located between a representative P-wave form factor histogram and a representative far field R-wave form factor histogram.

11. The method of claim 1, further comprising:

controlling the operation of the pulse generator based upon the representative form factor histogram such that the pacemaker properly paces and senses a heart of a patient.

12. A method of classifying signals sensed by an electrode of a medical electrical lead adapted to be positioned within an atrium of a heart of a patient, the lead forming a portion of a cardiac pacing system further comprising an implantable pulse generator for generating pacing pulses, the method comprising:

generating an interim form factor histogram which includes collected data points in the form of atrial event signal consisting of P-wave signals and far field R-wave signals;

adding the interim form factor histogram to a previously generated form factor histogram, the previously generated form factor histogram including previous collected data points, to create a representative form factor histogram; and classifying sensed signals as P-wave signals or far field R-wave signals based upon the representative form factor histogram.

13. The method of claim 12, wherein generating an interim form factor histogram further comprises:

collecting atrial event signals consisting of P-wave signals and far field R-wave signals;

rejecting atrial event signals if the pulse generator is not operating under normal conditions; and generating an interim form factor histogram based upon a form of collected atrial event signals which, the interim form factor histogram including an interim P-wave form factor histogram and an interim far field R-wave form factor histogram, each having bins of atrial event signals.

14. The method of claim 13, wherein collecting atrial event signals further comprises:

collecting atrial event signals consisting of P-wave signals and far field R-wave signals for a time interval in the range of 5–10 days.

15. The method of claim 13, wherein collecting atrial event signals further comprises:

collecting atrial event signals consisting of P-wave signals and far field R-wave signals for a time interval for approximately 30 minutes.

16. The method of claim 13, wherein rejecting atrial event signals further comprises;

rejecting atrial event signals if a tachycardia condition is sensed by the pulse generator.

17. The method of claim 13, wherein rejecting atrial event signals further comprises:

rejecting atrial event signals if interference is present within the pulse generator.

18. The method of claim 13, wherein rejecting atrial event signals further comprises:

rejecting atrial event signals if the pulse generator is in an AV asynchronous state.

19. The method of claim 12, wherein adding the interim form factor histogram to a previously generated form factor histogram further comprises:

discarding bins of atrial event signals within the interim form factor histogram which do not meet a discard level;

weighting a previously generated form factor histogram including a previously generated P-wave form factor histogram and a previously generated far field R-wave form factor histogram; and combining the weighted previously generated form factor histogram with the interim form factor histogram to create a representative form factor histogram.

20. The method of claim 19, wherein discarding bins of atrial event signals further comprises:

discarding bins of atrial events signals within the internal form factor histogram which do not meet a discard level such that approximately 0%–10% of the collected atrial event signals are discarded.

21. The method of claim 19, wherein weighting a previously generated form factor histogram further comprises:

multiplying a previously generated form factor histogram by a factor in the range of 0.25–0.90.

22. The method of claim 19, wherein weighting a previously generated form factor histogram further comprises:

multiplying a previously generated form factor histogram by a factor of 0.50.

23. The method of claim 12, wherein classifying sensed signals further comprises:

determining if a minimal safety margin is located between a representative P-wave form factor histogram and a representative far field R-wave form factor histogram within the representative form factor histogram.

24. The method of claim 12, further comprising:

controlling the pulse generator based upon the representative form factor histogram such that the pulse generator properly paces and senses the heart of the patient.

25. A cardiac pacing system for classifying signals sensed from within an atrium of a heart of a patient, the cardiac pacing system comprising;

a pulse generator for generating pacing pulses;

a medical electrical lead comprising an electrode, the lead being adapted to be positioned within the atrium of the heart of the patient and operably connected to the pulse generator for delivering pacing pulses to the heart;

a sense electrode adapted to be positioned within the atrium of the heart of the patient for sensing P-waves and far field R-waves; and a controller for generating a representative form factor histogram of the sensed P-waves and far field R-waves, for classifying sensed signals as P-wave signals or far field R-wave signals based up on the representative form factor histogram, and for controlling operation of the pulse generator based upon the representative form factor histogram.

26. The cardiac pacing system of claim 25, wherein the pulse generator further comprises an analog to digital converter for converting the sensed P-waves and far field R-waves into digital signals representing P-waves and far field R-waves.

27. The cardiac pacing system of claim 25, wherein the controller further comprises a microprocessor for generating the representative form factor histogram and for classifying sensed signals.

28. A signal classification system for classifying signals sensed by an electrode of a medical electrical lead adapted to be positioned within an atrium of a heart of a patient, the lead forming a portion of a cardiac pacing system further comprising a pulse generator for generating pacing pulses, the signal classification system comprising:

collecting means for collecting atrial event signals comprising P-wave signals and far field R-wave signals;

rejecting means for rejecting atrial event signals according to predetermined criteria;

generating means for generating an interim form factor histogram based upon a form of collected atrial event signals, the interim form factor histogram including an interim P-wave form factor histogram and an interim far field R-wave form factor histogram, each having bins of atrial event signals;

discarding means for discarding bins of atrial event signals within the interim form factor histogram which do not meet a discard level;

weighting means for weighting a previously generated form factor histogram including a previously generated P-wave form factor histogram and a previously generated far field R-wave form factor histogram;

generating means for combining the weighted previously generated form factor histogram with the interim form factor histogram to create a representative form factor histogram;

determining means for determining if a minimal safety margin is located between a representative P-wave form factor histogram and a representative far field R-wave form factor histogram within the representative form factor histogram; and classifying means for classifying atrial event signals as either P-wave signals or far field R-wave signals based upon the representative form factor histogram.

29. A cardiac pacing system for classifying signals sensed from within an atrium of a heart of a patient, the system comprising:

pulse generator means for generating pacing pulses;

stimulation electrode means adapted to be positioned within the atrium of the heart of the patient and in communication with the pulse generator for delivering pacing pulses to the heart;

sense electrode means adapted to be positioned within the atrium of the heart of the patient for sensing P-waves and far field R-waves; and controller means for generating a representative form factor histogram of the sensed P-waves and far field R-waves, for classifying sensed signals as P-wave signals or far field R-wave signals based upon the representative form factor histogram, and for controlling operation of the pulse generator based upon a form of the representative form factor histogram.

* * * * *